United States Patent [19]

Deans et al.

[11] Patent Number: 5,666,959
[45] Date of Patent: Sep. 16, 1997

[54] FETAL HEART RATE MONITORING

[75] Inventors: Anne Catherine Deans, Woking; Eric Serge Gilles Genevier, London; Philip James Steer, Surbiton, all of England

[73] Assignee: British Technology Group Limited, London, England

[21] Appl. No.: 520,774

[22] Filed: Aug. 30, 1995

[51] Int. Cl.$^6$ ................................................. A61B 5/0444
[52] U.S. Cl. ............................................................ 128/698
[58] Field of Search .................................... 128/630, 696, 128/698, 708, 901

[56] References Cited

U.S. PATENT DOCUMENTS

| | | | |
|---|---|---|---|
| 3,916,878 | 11/1975 | Courtin et al. | |
| 4,211,237 | 7/1980 | Nagel | 128/698 |
| 4,489,726 | 12/1984 | Epstein et al. | 128/630 |
| 4,951,680 | 8/1990 | Kirk et al. | 128/698 |
| 5,025,787 | 6/1991 | Sutherland et al. | |
| 5,042,499 | 8/1991 | Frank et al. | 128/698 |
| 5,123,420 | 6/1992 | Paret | |
| 5,372,139 | 12/1994 | Holls et al. | 128/698 |

FOREIGN PATENT DOCUMENTS

| | | |
|---|---|---|
| 2717530 | 10/1978 | Germany |
| 93/03669 | 3/1993 | WIPO |

OTHER PUBLICATIONS

G. Friesen et al, "A Comparison of the Noise Sensitivity of Nine QRS Detection Algorithms", IEEE Transactions on Biomedical Engineering vol. 37 No. 1, Jan. 1990, pp. 85–98.

*Primary Examiner*—Jeffrey R. Jastrzab
*Attorney, Agent, or Firm*—Cushman, Darby & Cushman IP Group of Pillsbury Madison & Sutro LLP

[57] ABSTRACT

A method and apparatus for deriving a pulse sequence corresponding to a fetal heart rate (FHR) from a composite ECG signal which includes a signal from a second source, such as from the mother or a twin. A peak detection technique is used to identify apparent QRS complex signal components in the composite ECG signal, which are then compared against a template by calculating a statistical correlation coefficient. If the correlation result exceeds a predetermined threshold, the complex is flagged as a match. The template is an adaptive one, and is initialized by taking the complexes associated with the first n peaks encountered in the composite ECG signal. It is then continuously updated with each QRS complex which provides an exceptional match. After event sorting and output validation, a sequence of pulses is produced which represents the fetal heartbeat and which can be passed to a conventional heart rate monitor for display. The maternal heart rate can be derived and monitored in the same way, a maternal template being created from identified complexes which fail the correlation against the fetal template. The apparatus and method are particularly applicable to a composite ECG signal monitored by way of an intrauterine probe which is non invasive to the fetus.

16 Claims, 7 Drawing Sheets

FETAL HEART RATE MONITORING

FIELD OF THE INVENTION

This invention relates to fetal heart rate monitoring, and more particularly, to a method and apparatus for deriving a pulse sequence corresponding to a fetal heart rate (FHR) from a composite EGG signal which includes a second source signal such as a maternal signal.

BACKGROUND OF THE INVENTION

It is highly desirable in obstetrics to provide information concerning the condition of the fetus both before and during labor. Fetal monitors have been developed for use in monitoring and recording both fetal heart rate and uterine activity.

Routine monitoring in labor currently relies on charting the fetal heart rate (FHR) and uterine contractions on a chart paper to produce a cardiotocogram (CTG). Measurement of these two variables can be made by way of either external or internal monitoring. In the case of external monitoring, Doppler ultrasound is used to detect fetal heart movements from which the heart rate can be derived, whilst an external tocodynamometer is used for the detection of uterine wall tension. However, the FHR and uterine activity measurement may be inaccurate and therefore in cases of high risk patients or suspected fetal compromise, internal monitoring is preferred.

In conventional internal monitoring techniques, a fetal scalp clip is attached to the skin of the fetal scalp. The fetal ECG is obtained from the scalp and detection of the QRS complexes enables measurement of the heart rate. An intrauterine pressure catheter for the direct measurement of intrauterine pressure (IUP) is also generally employed. This procedure necessitates the insertion of two devices, and mothers generally object to the use of a scalp clip piercing the skin of the baby. Furthermore, the scalp clip allows vertical transmission of viral infections from the mother to the baby (e.g. HIV or hepatitis B viruses).

More recent work in the field of internal monitoring has led to the development of a flexible intrauterine probe that lies alongside the fetus in utero. The probe is inserted transcervically in one single clinical procedure. It is fitted with surface electrodes which are in contact with the fetal head, along with an intrauterine pressure sensor. Such a probe is described in U.S. Pat. No. 5,025,787, a significant advantage of such a device being that it is non-invasive to the fetus (unlike both ultrasound and scalp clips) and requires minimal clinical procedure. The contents of U.S. Pat. No. 5,025,787 are included herein by reference.

The signal obtained by an intrauterine probe contains both the fetal and maternal ECG complexes. Such composite signals are incompatible with conventional cardiotocographs and it is therefore necessary to separate the maternal and fetal complexes to obtain an FHR recording. In the case of signals recorded by way of electrodes placed on the maternal abdomen, it is usually the case that the maternal complexes have an amplitude considerably greater than the fetal complexes, and this fact can be used for separation. In the case of signals recorded with an intrauterine probe no such assumption can be made. In some cases the maternal complexes are larger than the fetal ones, in others they are smaller or similar in size. Additionally, the polarity of both fetal and maternal complexes varies from one labor to the next, and sometimes during the course of a labor. It is to be noted that the abdominal ECG monitoring method referred to above suffers from the disadvantage that it usually cannot be used during labor, as the electromyographic signal from the uterine contractions often obscures the fetal ECG.

Techniques for deriving the FHR from a composite signal have been developed which rely on obtaining the maternal EGG from another source (e.g. maternal chest derived signals) and using this information to eliminate the maternal complexes by subtraction or by masking. However, such an approach suffers from the need for additional leads and electrodes placed on the maternal abdomen. These can be uncomfortable to the mother and can interfere with other clinical procedures during labor, especially if the monitoring lasts several hours or more. Furthermore, separate monitoring of the maternal ECG affords more scope for measurement errors to arise.

German patent application DE-A-2717530 discloses a proposed method of suppressing unwanted signal components in abdominally derived feto-maternal ECGs. This method involves preliminary filtering of the input signal, followed by the use of the cross correlation function between the filtered signal and a stored sample "interference signal". The interference signal identified is then subtracted from the composite signal. It is important to note that the method described depends on the maternal signal exhibiting a greater amplitude than the fetal signal, and that therefore signal amplitude threshold detectors can be used to identify the maternal QRS complexes (as explained above, such relative signal characteristics cannot be assumed in the case of signals derived from an intrauterine source). Once the maternal signal has been removed, the correlation analysis can be conducted to identify regularly occurring interference elements.

U.S. Pat. No. 5,123,420 describes a method for processing signals indicative of two or more heart rates (e.g. of two fetuses or of one fetus and its mother). The method relies on the detection of an FHR by means of a fetal scalp electrode or an ultrasound transducer, as well as the detection of a further fetal and/or a maternal heart rate by appropriate means. According to the technique, cross-correlation is used to compare two traces and provide a warning when coincidence is detected, thus warning that both detecting means are inadvertently recording the maternal trace and that consequently the fetal heart is not being monitored.

U.S. Pat. No. 5,025,787 makes reference to the fact that the maternal and fetal ECG complexes have different widths and generally different morphologies, and that this fact might be used to distinguish between them. It is suggested that frequency domain pattern recognition of the spectral components, or temporal/spatial pattern recognition, can be applied. However, the document does not teach a method which succeeds in providing effective discrimination between the signal components.

There therefore continues to exist a need to monitor the FHR by way of, for example, an intrauterine probe, which takes into account the maternal ECG contamination of the measured signal, without the need to additionally obtain the maternal ECG from another source. The end result for the clinical user should be a reliable and unambiguous FHR trace.

SUMMARY OF THE INVENTION

The separation of the composite signal into its components relies on the fact that the fetal and maternal ECG complexes have respectively different shapes, but takes into account the fact that these shapes can tend to progressively alter during monitoring.

According to the invention, there is provided a method for deriving a sequence of pulses corresponding to the heart rate of a fetus from a composite ECG signal which may include signals produced by a second source in addition to the desired fetal signals, the method comprising receiving a composite ECG signal having a repetitive fetal QRS complex signal component, identifying apparent QRS complex signal components using a peak detection process to locate significant peaks in the composite ECG signal, deriving from the identified apparent QRS complex signal components a template representing the fetal QRS complex signal component, calculating a statistical correlation coefficient between the identified apparent QRS complex signal components and the template, and deriving a sequence of pulses representing those QRS complex signal components which correlate with the template.

Preferably, from the identified apparent QRS complex signal components, a further template representing the second source QRS complex signal component is derived. A statistical correlation coefficient between the identified apparent QRS complex signal components and the further template is calculated, and a further sequence of pulses representing those QRS complex signal components which correlate with the further template is derived, the further sequence of pulses corresponding to the second source heart rate.

The composite EGG signal is preferably first filtered to remove fluctuations in the baseline prior to application of the peak detection process. It may then be subjected to non-linear compression to enhance the signal peaks prior to application of the peak detection process.

To improve the correlation step, the slope of the linear regression function between each identified apparent QRS complex signal components and the template is calculated, the slope being used for correlation purposes.

The template is preferably derived by storing a signal representative of the QRS complex signal components of the first n peaks located, and updating the stored signal with identified QRS complex signal components which show a sufficiently high correlation with the template. Preferably this step is carried out separately in respect of both the positive and the negative peaks located.

The peak of each identified QRS complex signal component is flagged according to the correlation result and the flags are sorted to retain only one flag per complex, the flags being used to derive the sequence of pulses corresponding to the fetal heart rate.

The time intervals between successive flags may be assessed against a reference interval value, and missing flags can thus be inserted where necessary. The reference interval value is preferably the median interval value between flags in a series of flags.

As a final sorting step, the series of flags is filtered by use of a moving median.

In a further aspect of the invention, there is provided a system which receives a composite ECG signal originating from a plurality of sources and which processes the signal to produce an output representative of one of the signal components, comprising a signal processing unit having an input coupled to receive a representation of the composite ECG signal, a peak detection data processing unit arranged to identify significant peaks in the composite ECG signal, a template buffer for storing a signal template derived from the composite EGG signal, which signal template represents a QRS complex of the the one signal component, a correlation data processing unit arranged to calculate a statistical correlation coefficient between the signal template and the waveform complexes of the composite ECG signal associated with the identified peaks, in order to identify those components which correlate with the signal template, and an output unit to produce an output signal representative of only the one the signal component.

BRIEF DESCRIPTION OF THE DRAWINGS

The invention will now be described, by way of example only, with reference to the accompanying drawings, in which.

DESCRIPTION OF THE PREFERRED EMBODIMENT

Figure 1:
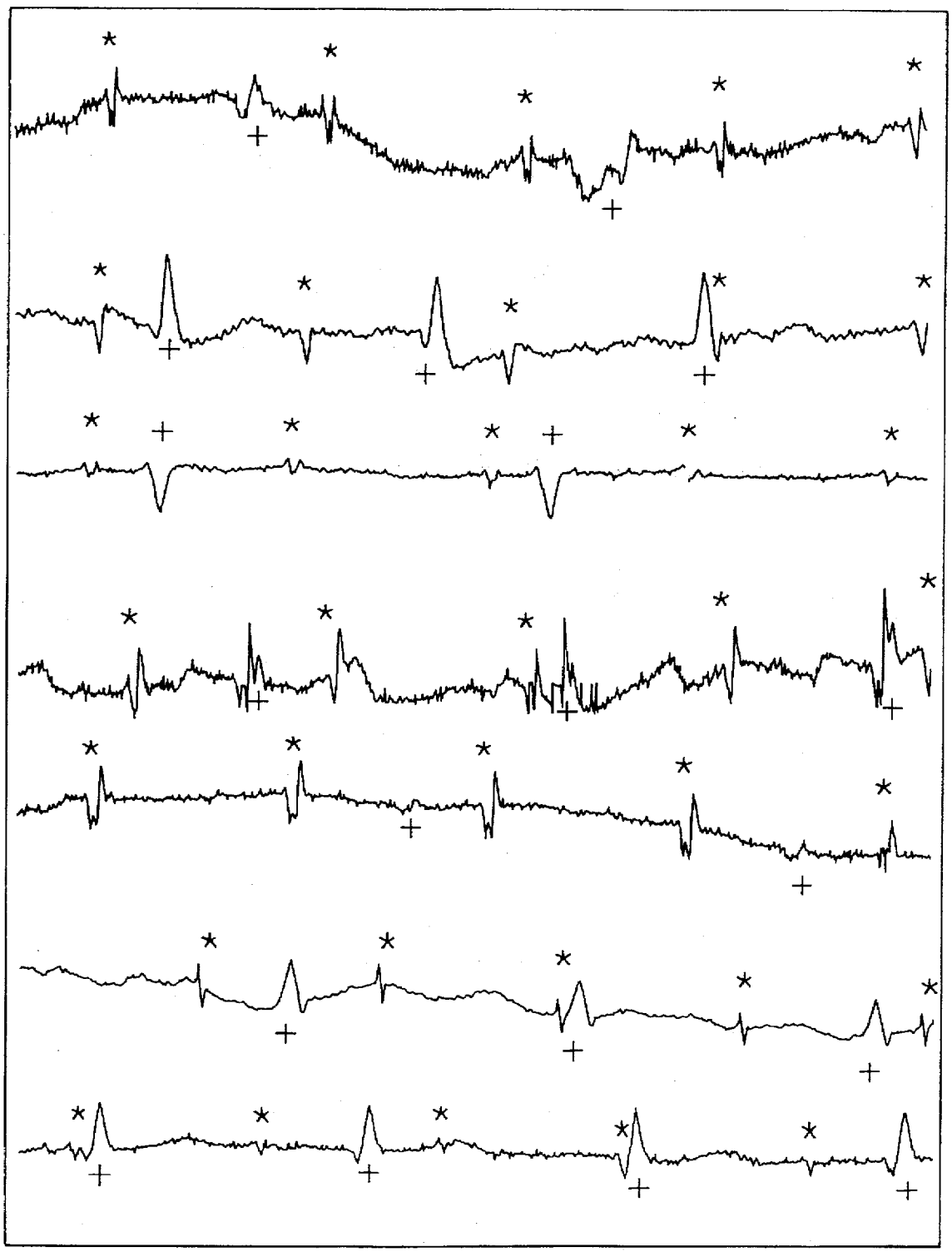
FIG. 1 shows examples of signals obtained with an intrauterine probe.

FIG. 1 illustrates a total of 7 traces of example composite ECG signals obtained by way of an intrauterine probe, such as that described in U.S. Pat. No. 5,025,787. It is to be noted that the symbols + indicate occurrences of maternal ECG complexes, whilst the * symbols indicate the fetal complexes. It can be seen that the morphologies, amplitudes and polarity of the traces vary enormously. In particular, the relative amplitudes of the two complexes are unpredictable, illustrating that, for signals obtained in this manner, this parameter is inherently unsuitable for use in discriminating between component signals.

Figure 2:
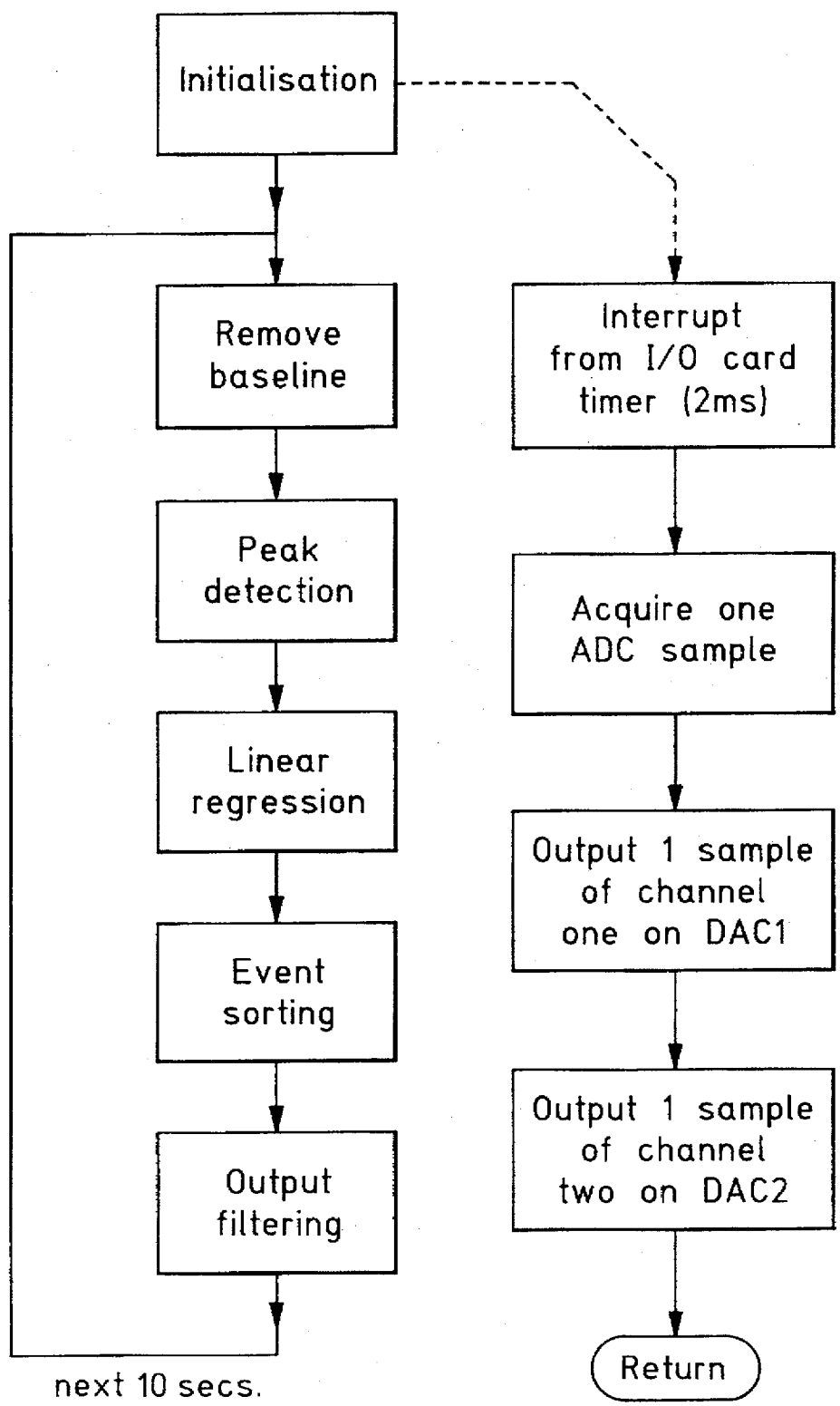
FIG. 2 shows a flow diagram of a method of processing according to the invention.
Figure 3A:
FIGS. 3a–3i illustrate the output signals from each stage of the method.

The flow diagram of FIG. 2 illustrates the main stages of a method used according to the present invention. The method used has six main stages: initialization, removal of baseline wander, detecting all complex peaks, detection of two populations of complexes, sorting the populations, and output filtering. Each stage will be described in more detail with reference to FIGS. 3a to 3i, which illustrate the output of each stage for a typical signal (FIG. 3a). Realization of the steps illustrated is carded out by software-controlled microprocessor signal processing, although it will be appreciated that the method of the invention may be realized using dedicated electronic circuitry. Appropriate elements of such circuitry will be familiar to the skilled person, who will be able to specify components depending on the circuit technology preferred.

The two types of complexes (fetal and maternal) will be referred to as population 1 and 2 and their polarity as positive or negative with respect to the signal baseline.

The intrauterine ECG signal is sampled at 500 Hz and stored in an array $X[x_n]$ of 5000 values. Ten seconds of data is processed while a further 10 seconds of data is acquired and stored.

Baseline removal

The first processing stage removes fluctuations in the baseline. The array $X[x_n]$ is processed three times by a third-order low-pass filter with a cut-off frequency of 25 Hz using the following equation:

$$b_n = 0.239 x_n + 0.76 b_{n-1}$$

Figure 3B:

The resulting value $b_n$ is then subtracted from the original value:

$$s_n = x_n - b_n$$

and stored in an array $S[s_n]$ (FIG. 3b).

Peak detection

Figure 3C:
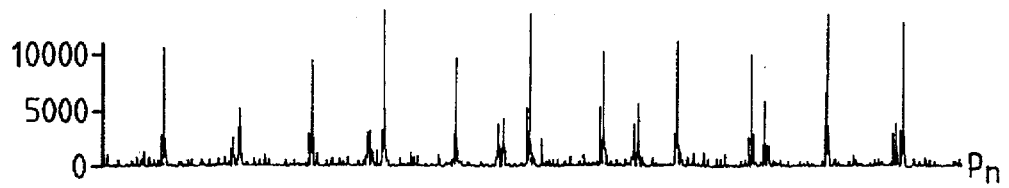

In order to detect the QRS peaks the signal array $S[s_n]$ is further processed to produce an array $P[p_n]$ using the following equation:

$$P_n = (s_{n+2} - s_{n-2})^2$$

where $s_n$ is the nth sample. Small changes (caused by noise) in the input signal are reduced and large changes such as those occurring during the QRS complex are enhanced (FIG. 3c). The next process consists of normalizing P by 'squashing it' non-linearly as follows:

$$q_n = \frac{1 + \sin\left(-\frac{\Pi}{2} + \Pi \cdot \frac{p_n}{\bar{p} \cdot 10}\right)}{2}$$

Where $\bar{p}$ is $$\bar{p} = \frac{1}{5000} \sum_{n=1}^{n=5000} p_n$$

Figure 3D:
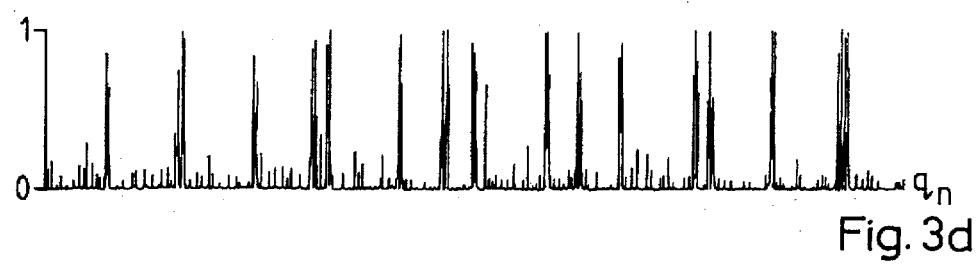
Figure 3E:
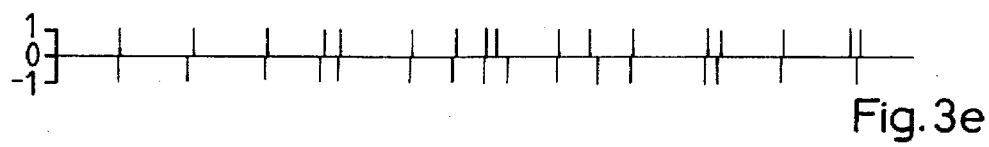

The array $Q[q_n]$ contains values between 0 and 1 (FIG. 3d). It is then scanned for peaks by identifying every value greater than 0.3. For each value found, the corrected signal array $S[s_n]$ is scanned from 10 points to the left of the location corresponding to the value 0.3 in $P[p_n]$ and 30 to the right, for the maximum and minimum values. These are flagged respectively as a positive peak and a negative peak (FIG. 3e).

The technique of peak detection described above has been specifically developed as being well suited to the method of the invention. However, a large variety of QRS detection techniques have been developed and such techniques may be equally appropriate for use in the method of the invention. The details of such procedures are known to those skilled in the art and will not be more closely described here. The article "A Comparison of the Noise Sensitivity of Nine QRS Detection Algorithms", Friesen et al, IEEE Transactions on Bimedical Engineering, Vol. 37, No. 1, January 1990, introduces nine different such algorithms and compares their sensitivity to noise corruption in received data.

Linear Regression Function

Figure 4:
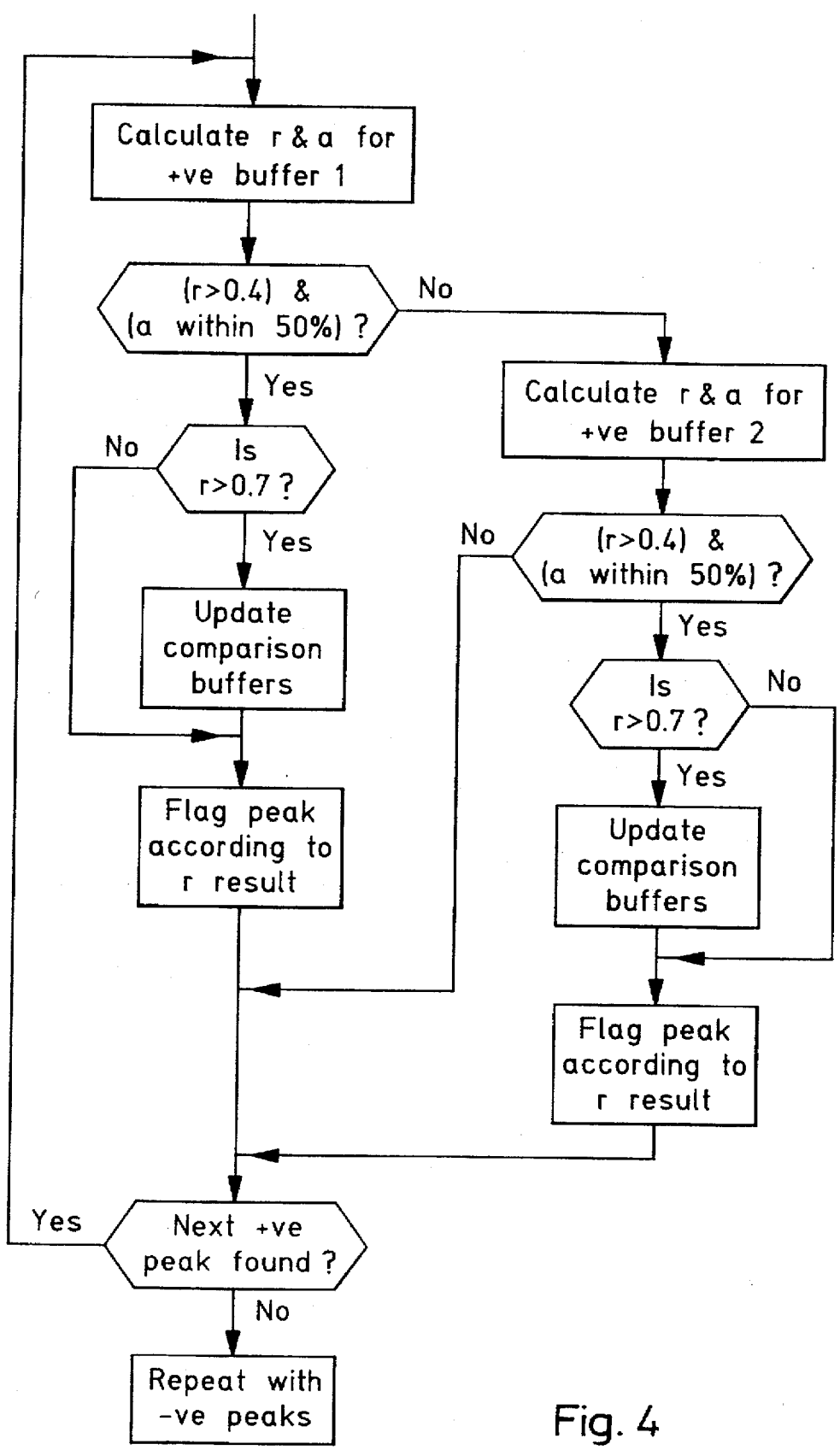
FIG. 4 shows a flow diagram of the linear regression function step of the method.

The flow diagram of the regression function is shown in FIG. 4. The method relies on the assumption that two different populations of ECG complexes are present. The inventors found that, surprisingly, the use of the linear regression function, and particularly the calculation of a statistical correlation coefficient, produces very good discrimination between the different QRS complex signal components for all tested examples of the signals encountered.

Four template buffers are used for the regression function. Each template consists of the average of the last 5 validated complexes of its type, and these last 5 complexes are also kept in the template buffer to continuously update the template during processing. Each template contains 50 values representing the following populations of complexes:

i. template 1—population 1, positive peak
ii. template 2—population 2, positive peak
iii. template 3—population 1, negative peak
iv. template 4—population 2, negative peak Each template is centered on its peak in the buffer. Initialization of the templates is described below.

Twenty five values to either side of the location of a detected positive peak in the input array $S[s_n]$ are compared with the first template contained in the first template buffer by calculating Pearson's statistical correlation coefficient, r:

$$r = \frac{\Sigma xy - n\bar{x}\bar{y}}{\sqrt{(\Sigma x^2 - n\bar{x}^2)(\Sigma y^2 - n\bar{y}^2)}}$$

Where $\bar{x}$ the mean of the x values, in this case the content of the template buffer 1; $\bar{y}$ is the mean of the y values, in this case the baseline corrected signal $S[s_n]$ centered on the detected peak; and n is 50. The slope a of the linear regression between the template and $S[s_n]$ is also calculated, as follows:

$$a = \frac{\Sigma xy - n\bar{x}\bar{y}}{\Sigma x^2 - n\bar{x}^2}$$

The buffer also contains the results of the slope calculations for the last 5 validated complexes (i.e. the 5 complexes contained in the buffer), as well as the average value of those last 5 results. The average value for template 1 is compared with the newly calculated slope. If the correlation coefficient is greater than 0.4 and the slope is within 50% of the average value, then the peak is flagged as a positive peak of population 1. If the correlation coefficient is greater than 0.7, the peak is used to update template 1 buffer and the regression slope buffer, and the peak is flagged as an excellent match. The updating of the buffer operates in a 'last in-first out' basis, to cater for changing morphologies in the trace. If the correlation coefficient is less than 0.4 or the difference in slope is too great (i.e. a is not within 50% of the buffer average value), then this process is repeated with template 2. Once the full 10 seconds have been processed, the correlation coefficient calculation and the regression function analysis is repeated using the negative buffers, templates 3 and 4. Each detected peak is therefore said to be of the same population as the template with which it best matches.

Figure 3F:
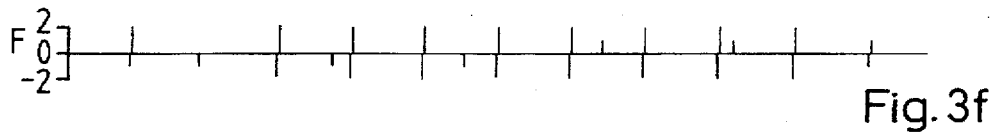
Figure 3G:
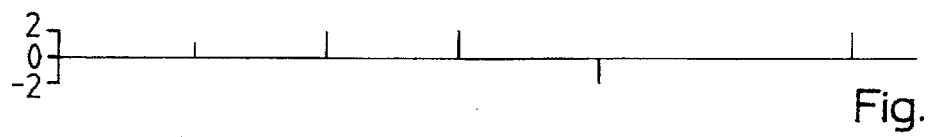

The output from this stage of the signal processing is two flag arrays, one per population (FIGS. 3f, 3g). Subsequently, the two populations are processed sequentially and independently.

Initialization

The initialisation consists of seeding the template and regression buffers. The first 5 positive and the first 5 negative peaks detected, regardless of whether they might belong to population 1 or 2, are averaged and loaded into template 1 and 3 buffers respectively. The next 5 positive and the next 5 negative peaks are then used to calculate the respective regression slopes with respect to these template buffers, the two results being loaded into the buffers as average regression slope values. The buffers for population 2 (templates 2 and 4) are initialized in the same manner, but only using the peaks that fail the regression analysis for population 1.

During the execution of the program the user can either reinitialize all the buffers, or the buffers of one of the two populations. This is usually only necessary at start-up, when the buffers have not immediately 'locked onto' the two populations, for example if operation commences during a period of noisy signal. In general, the inventors have found that this method of initialization produces very good results.

Event sorting and output validation

Figure 5:
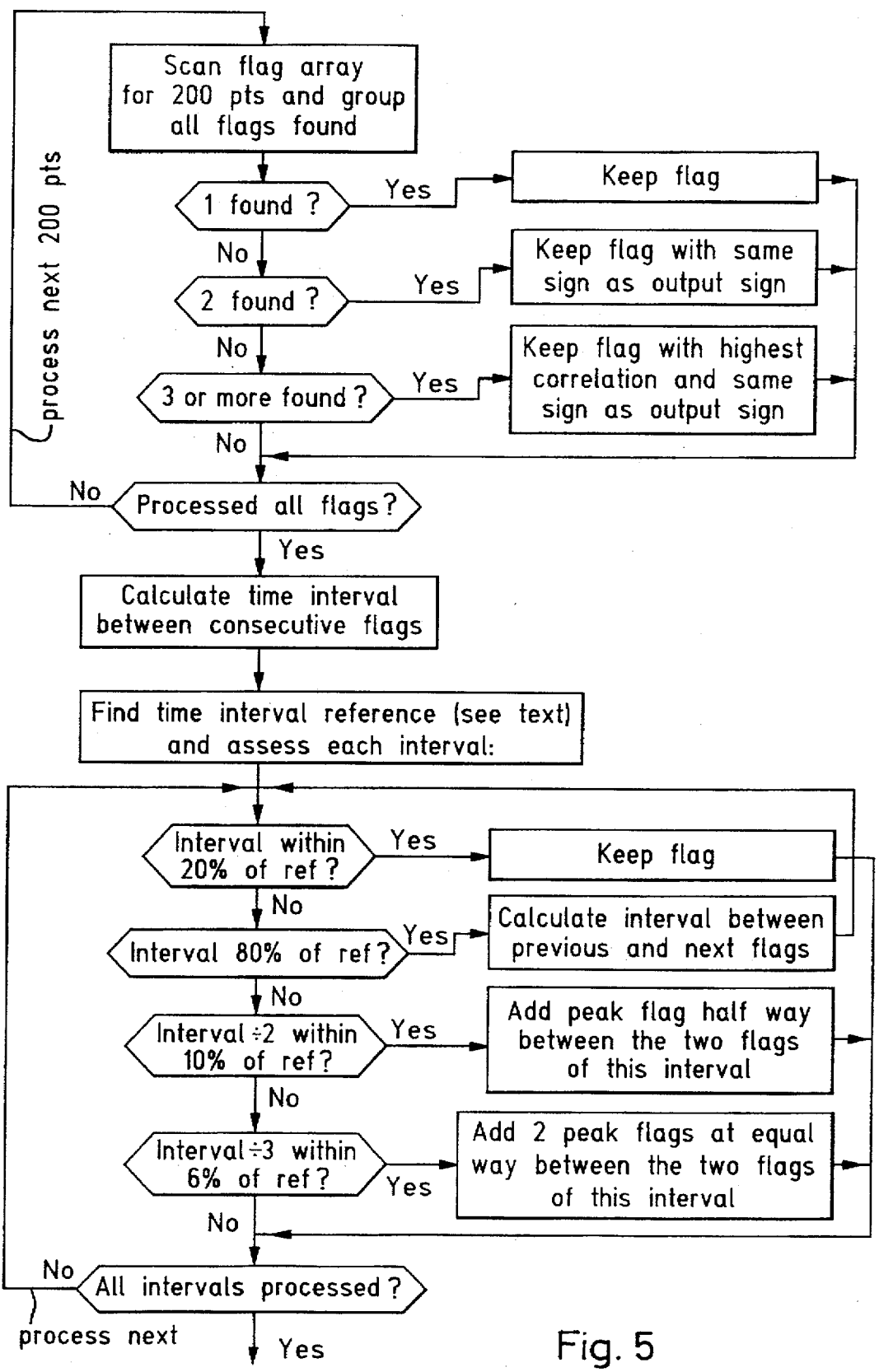
FIG. 5 shows a flow diagram of the event sorting function step of the method.

This part of the signal processing is required in order to be able to eliminate spurious flags resulting from the linear regression function. The flow diagram of the sorting function is shown in FIG. 5. The output from the regression function consists of two flag arrays, one array per population (FIG. 3f, 3g). Each datum in the array corresponds to the position of one sampled signal datum. It is zero if no correlation has been found; 1 and −1 for a poor correlation with respectively the positive and negative templates; and 2 or −2 for an excellent correlation with respectively the positive and negative templates.

These flags are grouped around each detected complex. For example, a bi-phasic complex would have a correlation with both positive and negative template buffers and in some occasions, even noise can correlate sufficiently with one template to be flagged. Only one flag per complex is kept for the subsequent processing. If two or more flags are set within 100 samples of one another, then the flag with the highest correlation (i.e. a 2 or −2 value) and with the same sign as the output sign is kept and the others are reset. The output sign is defined as the same sign as the template buffer with the highest absolute peak in its center. If one flag only is found, then it is retained.

Once the whole flag array has been processed, the sorting function calculates the time intervals between each flag and its preceding one and sorts the results. The median interval value is then taken as a reference and used to assess all the other time intervals against the following decisions. The median value is used as a reference, rather than the mean interval value, as the latter may be much lower than the actual heart rate interval. The decision steps are:

i. if the interval is within 20% of the reference (between 80% and 120% of the reference), then it is valid as a true interval.
ii. if the interval is less than 80% of the reference, then the time interval between the two flags on either side of the flag being tested are calculated and then entered in the decision loop. This serves to suppress spurious peaks due to noise or other artifact inadvertently flagged between successive true complexes.
iii. if half of the interval is within 10% of the reference, then another flag is set half way between the two flags, thus filling in erroneous gaps between flags.
iv. if one third of the interval is within 6% of the reference, then two other flags are set at regular intervals between the two flags, this also serving to infill missing flags.
v. if the flag failed all these tests, then it is kept, as it may be the initial value after a period of missing input data.

The last flag of a 10 second processing period is used as the first flag of the next 10 second period. The sorting process is the same for both populations.

Output filtering

The population of flags corresponding to the R-wave either of a maternal or fetal complex is then filtered by a sorting average. Each R-R interval in the 10 second period is calculated. For each interval, its value and the values of the two intervals either side are sorted in ranking order. The interval is then given the middle value. This step is illustrated in the table below. This technique is very valuable in removing so-called 'picket fencing', an event resulting from the misplacement of a QRS complex which results in one heart rate too long followed by another too short, or vice versa. On a CTG, this results in vertical bars which obscure the trace.

| Input rate | Rates used for filtering | Output rate |
|---|---|---|
|  | 118 |  |
| 119 | 119 | 119 |
|  | 121 |  |
|  | 119 |  |
| 121 | 121 | 120 |
|  | 120 |  |
| 120 | 121 |  |
|  | 120 | 120 |
|  | 109 |  |
|  | 120 |  |
| 109 | 109 | 120 |
|  | 133 |  |
|  | 109 |  |
| 133 | 133 | 121 |
|  | 121 |  |
|  | 133 |  |
| 121 | 121 | 121 |
|  | 119 |  |

Figure 3H:
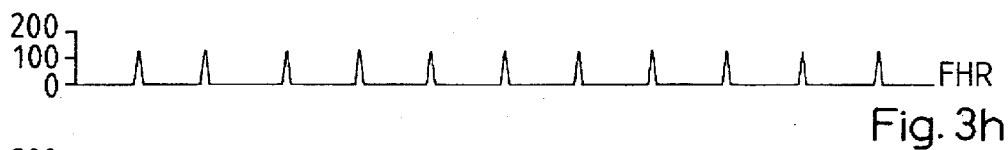
Figure 3I:
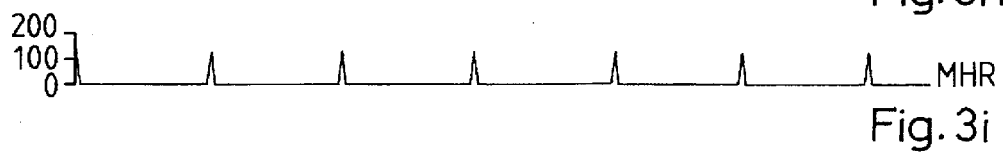

Two output signals, one for each population, are generated. These are illustrated in FIGS. 3h and 3i. The signals consist of 36 ms wide triangular waveforms centered at each R-wave position to simulate an ECG complex compatible with the input requirements of a conventional fetal monitor.

Implementation

An input/output board (model PC30D, Amplicon Liveline Ltd., Brighton, U.K.) is used in an IBM AT compatible personal computer. The PC30D has an on-board timer that generates interrupts every 2 ms. The interrupt servicing routine reads one input value from a 12 bit analogue to digital converter (ADC) and outputs two values, representing the simulated EGG waveforms of the two populations, to 2 digital to analogue converters (DAC). There are two buffers for the input signal; one containing 10 seconds of the current data and the other holds data which is being processed from the previous 10 seconds. Consequently, the data output is delayed by 20 seconds from real time. The output of the two DACs are attenuated and provide a simulated ECG waveform that can be connected to an Oxford Sonicaid Meridian dual-channel fetal monitor. One DAC is connected to the fetal ECG input and the other to the maternal ECG leads.

The execution time of the processing of the 10s data string ranges from 200 ms on 486DX2 based PC, to 6 seconds on a 286 based PC fitted with a 287 maths co-processor. Without a maths co-processor, the execution time is too long, for example 40 seconds on 486SX based PC.

Figure 6A:
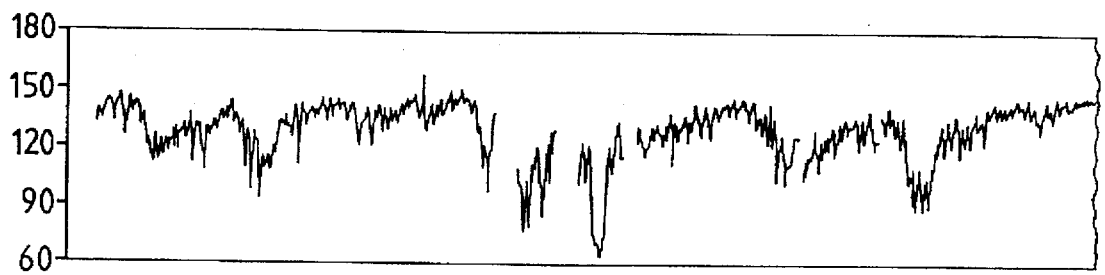
FIGS. 6a–6d show examples of typical CTG traces to illustrate the results of the method.
Figure 6B:
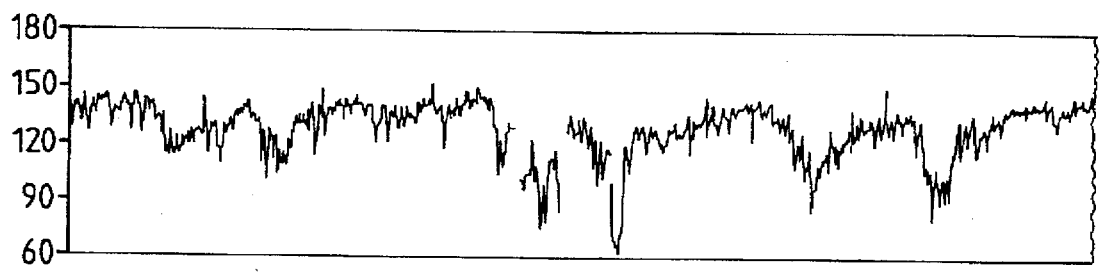
Figure 6C:
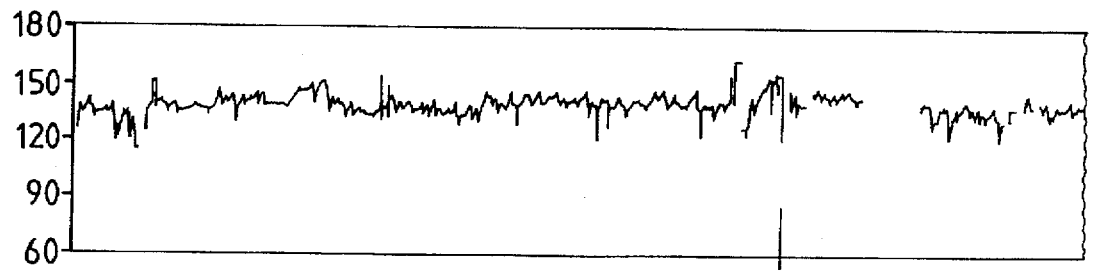
Figure 6D:
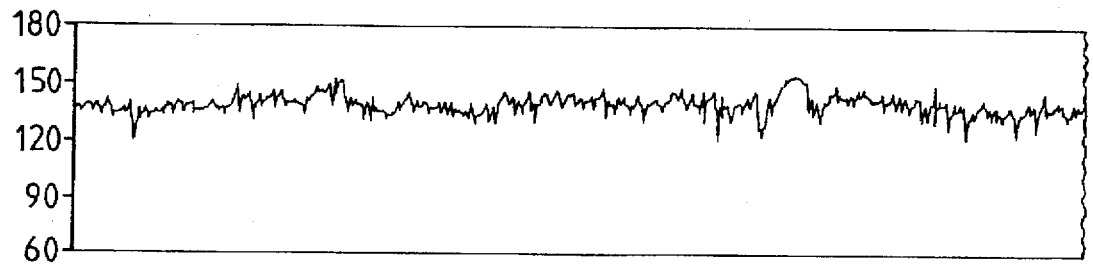

Signals from an intrauterine probe and simultaneous fetal ECG electrode (Copeland) were recorded on an FM tape recorder. These recordings were used for the development and testing of the technique and all data presented herein are derived from these tapes. Two examples of cardiotocograms (CTGs) obtained from the output of the apparatus of the invention compared with that from a conventional fetal electrode are shown in FIG. 6. FIGS. 6a and 6c show the FHR from a fetal scalp electrode, whilst FIGS. 6b and 6d respectively show the FHR derived by the method of the present invention.

The baseline removal step is not necessary for the peak detection but is preferable for the linear regression. The regression function correlates a data section of 100 ms duration and this is longer than the width of many complexes. It is therefore useful that the baseline is similar for all complexes as a fluctuating baseline will have an adverse effect on the regression results.

The initialization of the buffers used by the linear regression function is the only step that requires user intervention, and only when the initialization fails to lock on to one population of complexes. It is also possible to implement automatic reset procedures in the software, for example by detecting the absence of a coherent output using a quality control processor. It was found that the population with the highest rate normally seeded template 1 and 3 buffers, except in cases where the amplitude of the complexes of that population was much lower than those of the other population.

The use of the regression slopes is not an essential step, but is found to enhance the detection of complexes. It was observed that occasionally spikes in noisy signals have resulted in good correlations with the template buffers. Using the linear regression slopes in addition to the correlation coefficient has been found to eliminate most of these artifacts.

The output processing by the event sorter and the output filter are important features of the technique. The clinical interpretation of FHR patterns relies on a continuous recording. It only requires a few discontinuities and short periods of missing data for the FHR recording to be clinically unacceptable. Additionally it is important that three aspects of clinical interpretation of fetal heart rate patterns, baseline variability, accelerations and decelerations are reproduced accurately by the technique of the invention.

Locating the precise position of the R-wave when there is a coincidence of the fetal and maternal complex is problematical. One of the main difficulties in implementing an event sorter was to process the output of the regression function and establish which flag indicated the true rate. For example, when a complex was missed, because of a coincidence with a maternal complex, the rate calculated from the flags was halved. It is important to add an event between the two flags to ensure that appreciation of the FHR pattern is not obscured by spurious large fluctuations in rate. In order to determine that an event has been missed, it is necessary to know the range of rate which represents a true rate. The technique achieves this by sorting the rates and in effect establishing the rate probability density distribution with the median value representing the most frequent rate. When using the average rate (as opposed to the median) it was found that on some occasions, the output doubled or halved the true rate. Furthermore, the apparatus processes 10 seconds of data at a time because of the event sorter. A shorter block of data results in a poor rate probability density distribution, because fewer complexes are present; and a longer block of data implies that if a deceleration or acceleration occurs during the block of data being processed, some rates could be outside the reference rate range and yet still be valid rates.

The output filtering is the last step in producing a clinically readable trace. When a peak is misplaced by the operation of the apparatus, it results in two consecutive erroneous heart rates, one too short and the other too long. On the cardiotocogram, this results in the vertical spikes, of the afore-mentioned 'picket-fencing', degrading the quality of the trace. The output filter eliminates that effect without changing the heart rate pattern.

Figure 7A:
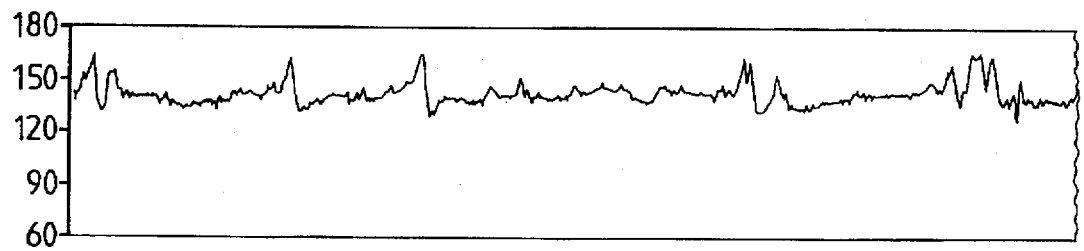
FIGS. 7a–7d demonstrate the effect of output filtering on CTG traces.
Figure 7B:
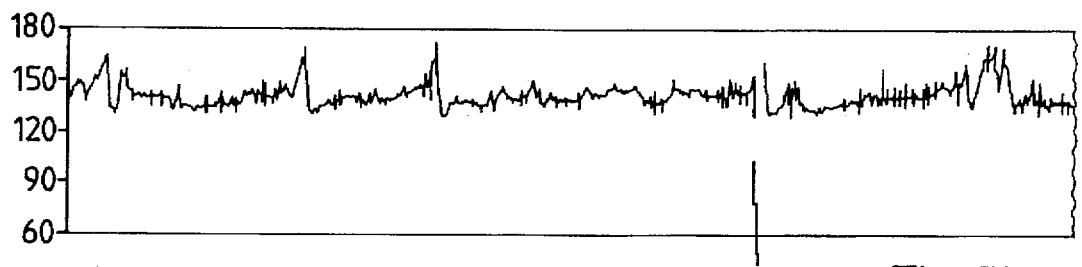
Figure 7C:
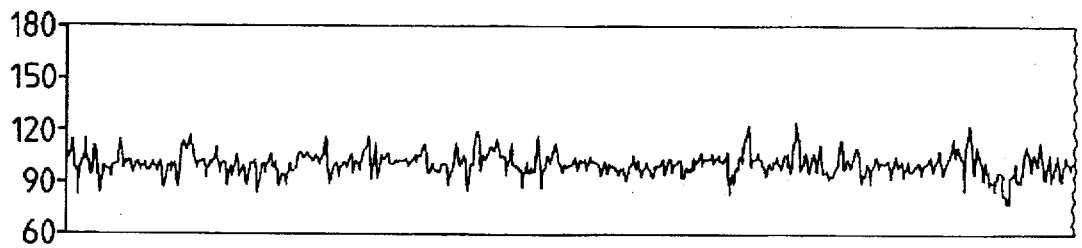
Figure 7D:
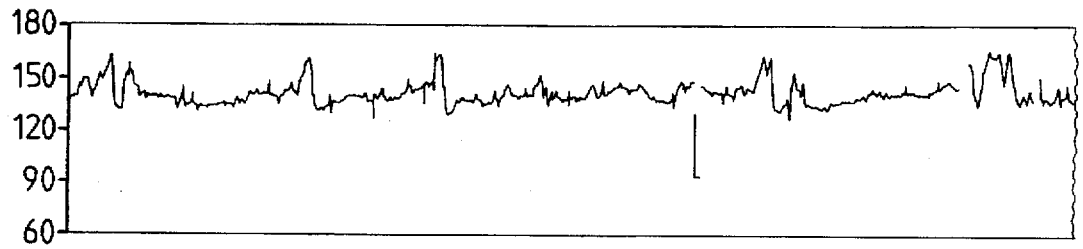

FIG. 7a shows the FHR from a fetal scalp electrode, whilst FIG. 7b shows the FHR derived by the method of the present invention; but without the inclusion of the output filtering step. 'Picket-fencing' occurred mainly during periods of relatively constant rate, when there are more coincidences between fetal and maternal complexes. During periods of rapidly changing rate, no artifact was seen. FIGS. 7c and 7d show respectively the maternal and the fetal heart rates as obtained using the method of the invention, including the output filtering. FIG. 7d shows that the 'picket-fencing' artifact was almost totally removed by the filtering without affecting the pattern of FHR variability, decelerations and accelerations.

The technique produced a cardiotocogram which was identical, for clinical purposes, with that produced from a simultaneously recorded signal from fetal ECG electrodes. It could of course be used for other similar applications, such as the separation of fetal and maternal signals obtained from abdominal electrodes or the separation of two fetal signals in the case of twins. It is to be noted that the method of the invention is effective even in cases where the second source (e.g. maternal) complexes are not present or are too small to be detected.

In the case of signals derived from a probe such as that described in U.S. Pat. No. 5,025,787, which incorporates a number of electrodes in different positions along the length of the probe body, the best signal may be identified in order to select the electrode whose signal is to be processed by the method of the invention. If initialization proves difficult, a quality control processor may implement selection of an alternative electrode whose signal is more readily separated into its components. The quality control processor may also serve to automatically reinitialize the template buffers after an appropriate time (for example 1 minute) if a viable template is not created.

We claim:

1. A method for deriving a sequence of pulses corresponding to a heart beat of a fetus from a composite ECG signal which may include signals produced by a second source heart beat in addition to desired fetal signals, said method comprising:

receiving a composite ECG signal having a repetitive fetal QRS complex signal component;

identifying apparent QRS complex signal components using a peak detection process to locate significant peaks in said composite ECG signal;

deriving from said identified apparent QRS complex signal components a template representing a fetal QRS complex signal component;

calculating a statistical correlation coefficient between all of said identified apparent QRS complex signal components and said template; and deriving a sequence of pulses corresponding to said heart beat of said fetus from those identified apparent QRS complex signal components which correlate with said template.

2. A method according to claim 1, further comprising:

deriving, from said identified apparent QRS complex signal components, a further template representing a QRS complex signal component from said second source heart beat;

calculating a statistical correlation coefficient between said identified apparent QRS complex signal components and said further template; and deriving a further sequence of pulses representing those identified apparent QRS complex signal components which correlate with said further template, said further sequence of pulses corresponding to said second source heart beat.

3. A method according to claim 1, further comprising:

low-frequency filtering said composite ECG signal to remove low frequency fluctuations prior to use of said peak detection process.

4. A method according to claim 1, further comprising:

subjecting said composite ECG signal to a non-linear compression to enhance signal peaks prior to use of said peak detection process.

5. A method according to claim 1, further comprising:

deriving a linear regression function between said identified apparent QRS complex signal components and said template;

calculating a slope value of said linear regression function; and using said slope value to verify said identified apparent QRS complex signal components which correlate with said template.

6. A method according to claim 1, wherein:

said identified apparent QRS complex signal components includes at least a first number n peaks; and said template is derived by:
storing at least one signal representative of said identified apparent QRS complex signal components of said first number n peaks located, and
updating said stored at least one signal with identified apparent QRS complex signal components which correlate with said template.

7. A method according to claim 1, wherein:

said identified apparent QRS complex signal components includes at least a first number n1 of positive peaks and at least a first number n2 of negative peaks; and wherein said deriving step comprises deriving first and second fetal templates from said identified apparent QRS complex signal components;

said first fetal template being derived by:
storing, as said first fetal template, a first signal representative of identified apparent QRS complex signal components of said first number $n_1$ of positive peaks located,
updating said first fetal template with identified apparent QRS complex signal components which correlate with said first fetal template; and said second fetal template being derived by:
storing, as said second fetal template, a second signal representative of said identified apparent QRS complex signal components of said first number $n_2$ of negative peaks located, and
updating said second fetal template with identified apparent QRS complex signal components which correlate with said second fetal template.

8. A method according to claim 7, wherein:

$n_1=n_2$; and
$4 \leq n_1 \leq 6$.

9. A method according to claim 1, further comprising:

flagging a peak of each identified apparent QRS complex signal component with a corresponding flag according to said statistical correlation coefficient; and sorting said flags to retain only one flag per apparent QRS complex signal component, said flags being used to derive said sequence of pulses corresponding to said heart beat of said fetus.

10. A method according to claim 9, further comprising:

assessing time intervals between successive ones of said flags against a reference interval value; and inserting missing flags where necessary.

11. A method according to claim 10, wherein:

said reference interval value is a median interval value between flags in a series of said flags.

12. A method according to claim 9, further comprising:

filtering said flags by use of a moving median.

13. A system for processing a composite ECG signal to produce an output representative of one signal component of said composite ECG signal, comprising:

means for receiving said composite ECG signal originating from a plurality of sources;

a signal processing unit having an input coupled to receive a representation of said composite ECG signal;

a peak detection data processing unit arranged to identify significant peaks in waveform complexes in said composite ECG signal;

a template buffer to store a signal template derived from said composite ECG signal, said signal template representing a QRS complex of said one signal component;

a correlation data processing unit arranged to calculate a statistical correlation coefficient between said signal template and all waveform complexes of said composite ECG signal associated with said identified peaks, in order to identify those components of said composite ECG signal which correlate with said signal template; and an output unit to produce an output signal representative of only said one signal component.

14. A system according to claim 13, wherein:

said means for receiving said composite ECG signal is an intrauterine ECG probe coupled to said signal processing unit, said intrauterine ECG probe detecting said composite ECG signal and providing said composite ECG signal to said signal processing unit.

15. A system for processing a composite ECG signal to produce an output representative of one signal component of said composite ECG signal, comprising:

a probe to generate a composite ECG signal;

a signal processing unit having an input coupled to receive a representation of said composite ECG signal;

a peak detection data processing unit arranged to identify significant peaks in waveform complexes in said composite ECG signal;

a template buffer for storing a signal template derived from said composite ECG signal, said signal template representing a QRS complex of said one signal component;

a correlation data processing unit arranged to calculate a statistical correlation coefficient between said signal template and all waveform complexes of said composite ECG signal associated with said identified peaks, in order to identify those components of said composite ECG signal which correlate with said signal template; and an output unit to produce an output signal representative of only said one signal component.

16. A system for processing a composite ECG signal to produce an output representative of one signal component of said composite ECG signal, comprising:

probe means for generating a composite ECG signal;

signal processing means for receiving a representation of said composite ECG signal;

peak detection data processing means for identifying significant peaks in waveform complexes in said composite ECG signal;

template buffer means for storing a signal template derived from said composite ECG signal, said signal template representing a QRS complex of said one signal component;

correlation data processing means for calculating a statistical correlation coefficient between said signal template and all waveform complexes of said composite ECG signal associated with said identified peaks, and for identifying those components of said composite ECG signal which correlate with said signal template; and output means for producing an output signal representative of only said one signal component.

* * * * *